(12) United States Patent
Beard et al.

(10) Patent No.: US 6,348,792 B1
(45) Date of Patent: Feb. 19, 2002

(54) SIDE-LOOKING NMR PROBE FOR OIL WELL LOGGING

(75) Inventors: David Beard; Arcady Reiderman, both of Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 09/677,359

(22) Filed: Oct. 2, 2000

Related U.S. Application Data

(60) Provisional application No. 60/221,078, filed on Jul. 27, 2000.

(51) Int. Cl.[7] .................................................. G01V 3/00
(52) U.S. Cl. ......................... 324/303; 324/300; 324/307
(58) Field of Search ................................ 324/303, 300, 324/318, 307, 309, 322

(56) References Cited

U.S. PATENT DOCUMENTS

| 4,350,955 A | 9/1982 | Jackson et al. ............. 324/303 |
|---|---|---|
| 4,717,877 A | 1/1988 | Taicher et al. .............. 324/303 |
| 5,055,787 A | 10/1991 | Kleinberg et al. .......... 324/303 |
| 5,488,342 A | 1/1996 | Hanley ........................ 335/306 |
| 5,646,528 A | 7/1997 | Hanley ........................ 324/303 |
| 6,023,164 A | 2/2000 | Prammer .................... 324/303 |

*Primary Examiner*—Hezron Williams
*Assistant Examiner*—Brij B. Shrivastav
(74) *Attorney, Agent, or Firm*—Madan, Mossman & Sriram, P.C.

(57) ABSTRACT

A side-looking NMR logging tool incorporates a permanent magnet arrangement having a magnetization direction oriented towards a side of the tool and a dipole RF antenna displaced towards the front of the tool. The magnet arrangement produces a shaped region of investigation in front of the tool wherein the magnetic field has a uniform field strength and the RF field has a uniform field strength in a direction orthogonal to the static field. The shaping of the static field is accomplished by the magnet arrangement comprising a plurality of magnets having parallel magnetization or by a single shaped magnet. The antenna arrangement includes a gapped core made of non-ferritic soft material for increasing the antenna efficiency. The magnet arrangement also reduces ringing in the core and the antenna. An optional RF shield is used to reduce NMR signals from borehole fluids.

36 Claims, 6 Drawing Sheets

SIDE-LOOKING NMR PROBE FOR OIL WELL LOGGING

CROSS REFERENCES TO RELATED APPLICATIONS

This applications claims priority from U.S. Provisional Patent Application Ser. No. 60/221,078 filed on Jul. 27, 2000.

FIELD OF THE INVENTION

This invention relates to apparatus and techniques for making nuclear magnetic resonance (NMR) measurements in boreholes, and to methods for determining magnetic characteristics of formations traversed by a borehole. Specifically, the invention relates to a side-looking NMR tool that attenuates NMR signals from the borehole while maintaining a large region of investigation within the formation.

BACKGROUND OF THE INVENTION

A variety of techniques have been used in determining the presence and in estimating quantities of hydrocarbons (oil and gas) in earth formations. These methods are designed to determine formation parameters, including among other things, porosity, fluid content, and permeability of the rock formation surrounding the wellbore drilled for recovering hydrocarbons. Typically, the tools designed to provide the desired information are used to log the wellbore. Much of the logging is done after the well bores have been drilled. More recently, wellbores have been logged while drilling of the wellbores, which is referred to as measurement-while-drilling ("MWD") or logging-while-drilling ("LWD"). Measurements have also been made when tripping a drillstring out of a wellbore: this is called measurement-while-tripping ("MWT").

One recently evolving technique involves utilizing Nuclear Magnetic Resonance (NMR) logging tools and methods for determining, among other things porosity, hydrocarbon saturation and permeability of the rock formations. The NMR logging tools are utilized to excite the nuclei of the fluids in the geological formations in the vicinity of the wellbore so that certain parameters such as spin density, longitudinal relaxation time (generally referred to in the art as "$T_1$"), and transverse relaxation time (generally referred to as "$T_2$") of the geological formations can be estimated. From such measurements, porosity, permeability, and hydrocarbon saturation are determined, which provides valuable information about the make-up of the geological formations and the amount of extractable hydrocarbons.

A typical NMR tool generates a static magnetic field $B_0$ in the vicinity of the wellbore, and an oscillating field $B_1$ in a direction perpendicular to $B_0$. This oscillating field is usually applied in the form of short duration pulses. The purpose of the $B_0$ field is to polarize the magnetic moments of nuclei parallel to the static field and the purpose of the $B_1$ field is to rotate the magnetic moments by an angle θ controlled by the width $t_p$ and the amplitude $B_1$ of the oscillating pulse. For NMR logging, the most common sequence is the Carr-Purcell-Meiboom-Gill ("CPMG") sequence that can be expressed as $$TW-90-(t-180-t-echo)_n \qquad (1)$$

where TW is a wait time, 90 is a 90 degree tipping pulse, 180 and is a 180 degree refocusing pulse.

After being tipped by 90°, the magnetic moment precesses around the static field at a particular frequency known as the Larmor frequency $\omega_0$, given by $\omega_0 = \gamma B_0$, where $B_0$ is the field strength of the static magnetic field and γ is the gyromagnetic ratio. At the same time, the magnetic moments return to the equilibrium direction (i.e., aligned with the static field) according to a decay time known as the "spin-lattice relaxation time" or $T_1$. Inhomogeneities of the $B_0$ field result in dephasing of the magnetic moments and to remedy this, a 180° pulse is included in the sequence to refocus the magnetic moments. This gives a sequence of n echo signals. These echo sequences are then processed to provide information about the relaxation times.

U.S. Pat. No. 4,350,955 to Jackson et al discloses a pair of permanent magnets arranged axially within the borehole so their fields oppose, producing a region near the plane perpendicular to the axis, midway between the sources, where the radial component of the field goes through a maximum. Near the maximum, the field is homogeneous over a toroidal zone centered around the borehole. With the Jackson arrangement, the axial extent of the region of examination is quite limited. As a result of this, the device can only be operated at relatively low logging speeds: otherwise, because of the tool motion during logging, the magnitude of the static field changes significantly within a fixed region of the formation with an accompanying degradation of NMR signals.

There are three approaches that may be taken in the design of an eccentric logging tool. One approach is to have a static field defining a region of examination that is primarily on one side of the tool. A second approach is to have a RF antenna that is primarily sensitive to signals from one side of the tool. The third approach is to have both the static field and the RF antenna with directional sensitivity.

U.S. Pat. No. 5,488,342, to Hanley, discloses a variation of the Jackson device wherein a shaping magnet is positioned adjacent the space between the pair of opposed magnets with its magnetic axis transverse to the borehole axis. The arrangement in the Hanley '342 patent has a region of uniform static field that is limited to one side of the magnet arrangement. U.S. Pat. No. 5,646,528 also to Hanley, discloses another variation of the Jackson device in which a shield of electrically conductive material is positioned adjacent to and laterally offset from the set of electrical coils whereby the magnetic field generated by the RF antenna is asymmetrically offset from the axis of the first magnets. The region of uniform static field remains a toroid, as in the Jackson device. The Hanley '528 device may be operated eccentrically within a large borehole with a reduction in the borehole signal. Both of the Hanley devices suffer from the drawback that the axial extent of the region of examination is small, so that they cannot be operated at high logging speeds.

There are several devices in which the problem of limited axial extent of the basic Jackson configuration of permanent magnets is addressed. U.S. Pat. No. 4,717,877 to Taicher et al teaches the use of elongated cylindrical permanent magnets in which the poles are on opposite curved faces of the magnet. The static field from such a magnet is like that of a dipole centered on the geometric axis of the elongated magnets and provides a region of examination that is elongated parallel to the borehole axis. The RF coil in the Taicher device is also a dipole antenna with its center coincident with the geometric axis of the magnet, thereby providing orthogonality of the static and magnetic field over a full 360° azimuth around the borehole.

U.S. Pat. 6,023,164 to Prammer discloses a variation of the Taicher patent in which the tool is operated eccentrically within the borehole. In the Prammer device, NMR logging probe is provided with a sleeve having a semi-circular RF shield covering one of the poles of the magnet: the shield blocks signals from one side of the probe. The probe is provided with elements that press the uncovered side of the probe to the sidewall of the borehole so that signals from the uncovered side arise primarily from the formation.

For both the Prammer and the Hanley '528 devices, in order to get the best attenuation in the field behind the probe while maintaining sensitivity in front of the probe, the shield should be positioned as far away from the front region as possible. The effectiveness of the shield is limited by the diameter of the tool. In the absence of a shield, the Prammer and Hanley '528 tools have a circular sensitive region, so that use of either device in an eccentric manner would result in a large signal from the borehole fluid.

U.S. Pat. No. 5,055,787 to Kleinberg et al combines the RF shield concept taught in Prammer with a shaping of the static field and with actually separating the effective center of the RF dipole antenna and the center of the magnet arrangement. Three magnets with parallel magnetization are used to produce the static field, the center magnet being opposed in polarity to the magnets on either side. The device has a region in front of the tool with a zero gradient while the region behind the tool has a large gradient. Consequently, the volume of the sensitive region in front of the tool is much larger than the sensitive region behind the tool, so that borehole signals are greatly reduced. One drawback of the Kleinberg arrangement is that the region of examination is very close to the tool. This makes it difficult to make measurement deeper into the formation, a serious drawback if there is significant invasion of the formation by borehole fluids. The Kleinberg device is also what is known as a zero gradient tool, i.e., the static field has substantially zero gradient in the region of examination. This is a disadvantage in NMR logging because many interpretation techniques for deriving petrophysical information about fluid diffusion in the formation from NMR data depend upon having a known and finite gradient.

SUMMARY OF THE INVENTION

The present invention is a side-looking NMR probe for well logging applications. It incorporates a number of design features, some of which are novel in themselves, in a novel combination that greatly improves the effectiveness of the tool. The starting point is a configuration that includes a static field similar to that of a dipole, and a dipole-like RF field substantially orthogonal to the static field, with the centers of the equivalent static and RF dipoles laterally displaced to provide a match on a side defined as the front of the tool and a mismatch on the back of the tool. The basic static field may be produced by a main magnet. The static field in the region of investigation has a field strength within predetermined limits and a substantially uniform gradient. Those versed in the art would recognize that in a so-called zero gradient logging tool, in contrast, the static field in the region of investigation has a substantially uniform field strength around a saddle point. A second, shaping magnet is used to shape the static field to conform to the RF field over a larger azimuthal sector around the tool. The RF field is also shaped to increase the effective radius in the front of the tool, giving a greater depth of penetration, and making it conform to the static field over a larger azimuthal sector. The antenna dipole is configured with as large a dipole as possible, thereby increasing its efficiency. A static shield may be used to reduce the RF field behind the tool. The static and RF dipoles are rotated 90° relative to prior art, so that the static dipole points to the side of the tool and the RF dipole to the front of the tool. With this arrangement, eddy currents in the shield are substantially increased, increasing its effectiveness. The RF antenna includes a core made of a soft magnetic material to increase its efficiency. The shaping magnet also acts as a bucking magnet to allow use of the core material: in its absence, the static field would be shorted out due to the rotated field orientation. This greatly reduces the field in the core and hence also reduces magnetostrictive ringing. In addition, the ringing in the core is reduced by using a soft magnetic material comprising particles of powdered material small enough to be transparent to the RF magnetic field

DESCRIPTION OF THE PREFERRED EMBODIMENT

Figure 1:
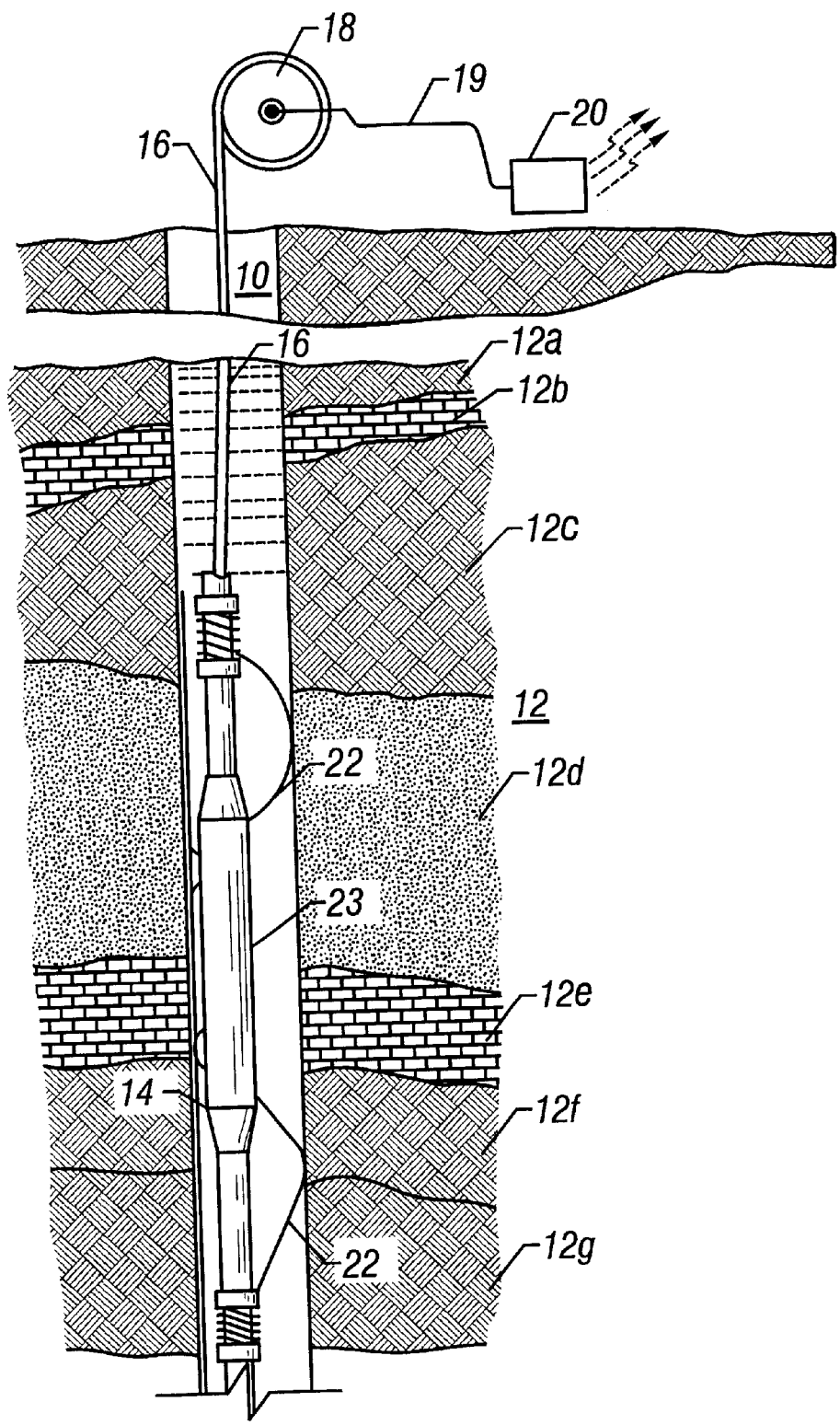
FIG. 1 depicts diagrammatically an eccentric NMR logging tool in a borehole.

FIG. 1 depicts a borehole 10 which has been drilled in a typical fashion into a subsurface geological formation 12 to be investigated for potential hydrocarbon producing reservoirs. An NMR logging tool 14 has been lowered into the hole 10 by means of a cable 16 and appropriate surface equipment represented diagrammatically by a reel 18 and is being raised through the formation 12 comprising a plurality of layers 12a through 12g of differing composition, to log one or more of the formation's characteristics. The NMR logging tool is provided with bowsprings 22 to maintain the tool in an eccentric position within the borehole with one side of the tool in proximity to the borehole wall. The permanent magnets used for providing the static magnetic field is indicated by 23 and the magnet configuration is that of a line dipole. Signals generated by the tool 14 are passed to the surface through the cable 16 and from the cable 16 through another line 19 to appropriate surface equipment 20 for processing, recording and/or display or for transmission to another site for processing, recording and/or display.

Figure 2:
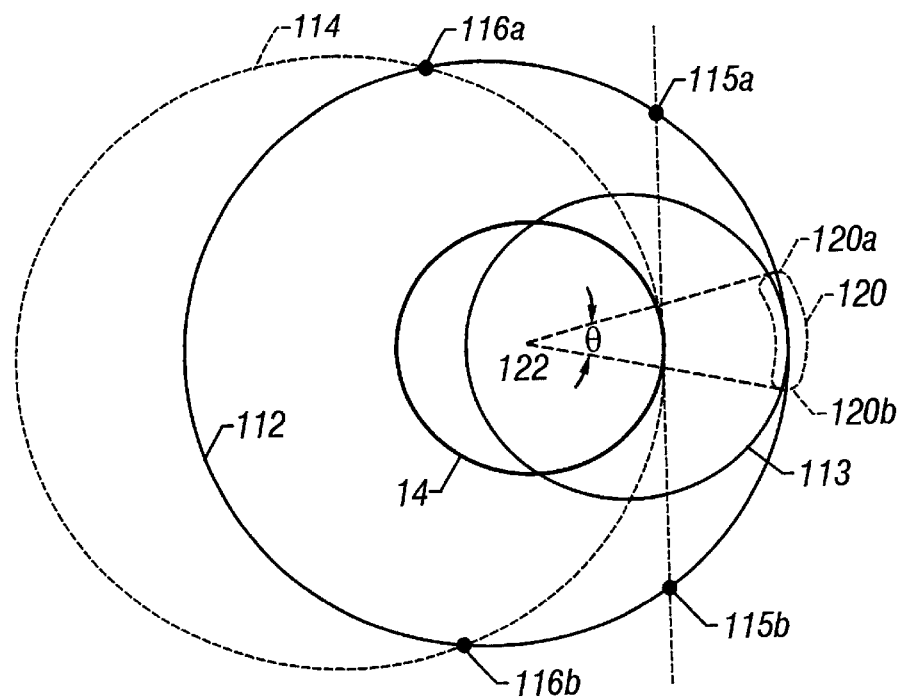
FIG. 2 shows the field distributions for an eccentric logging tool with separated RF and static dipoles.

Turning now to FIG. 2, the RF and static fields isolines are illustrated for a configuration comprising separated RF and static 2D dipoles placed inside a NMR probe 14 eccentrically located within a borehole 114. For simplifying the illustration, the locations of the centers of the RF and static 2D dipoles are not shown. As shown in FIG. 2, the difference in curvature of the static 112 and RF 113 magnetic field isolines creates a mismatch which rapidly increases with the departure from the central point of the region of examination 120. The region of examination 120 subtends only a small angle θ at the center 122 of the tool 114.

The maximum volume possible for acquiring a NMR signal from the formation in the side-looking tool may be extended up to the boundary of the borehole 114. Preferably, the arc of the working region 120 extends so that the end 120a lies between points 115a and 116a in FIG. 2 and the end 120b lies between the points 115b and 116b. This extension takes into account the largest boreholes and even possible washouts. When the working region extends to points 115a, 115b, and when the radius of the tool equals the depth of the working region into the formation, the angle θ would be 120°. For most applications, the angle θ lies between 90° and 135°.

Figure 2A:
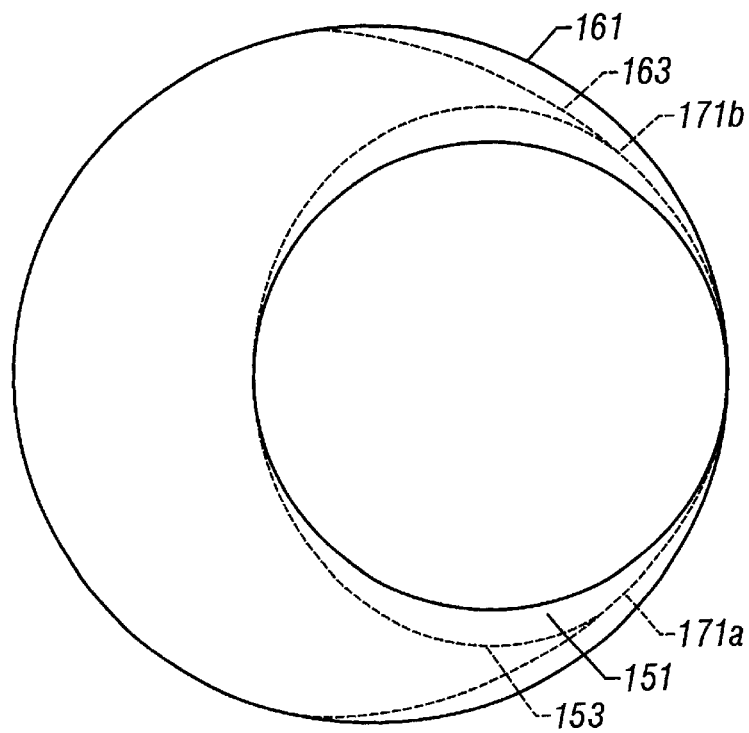
FIG. 2A illustrates a desired field configuration of static and RF fields for a side-looking NMR device.

FIG. 2A shows desired field configurations for the static and RF fields in a side-looking NMR device. Shown are isolines in cross section for the static 161 and RF 151 fields corresponding to offset dipoles. The desired field configuration has the elongate oval or pear shaped isoline 163 for the static field and the flattened oval shaped isoline 153 for the RF field. where the RF and the static isolines match over the arcuate segment 171a–171b. This defines the region of investigation that may be used in NMR investigations.

Figure 3:
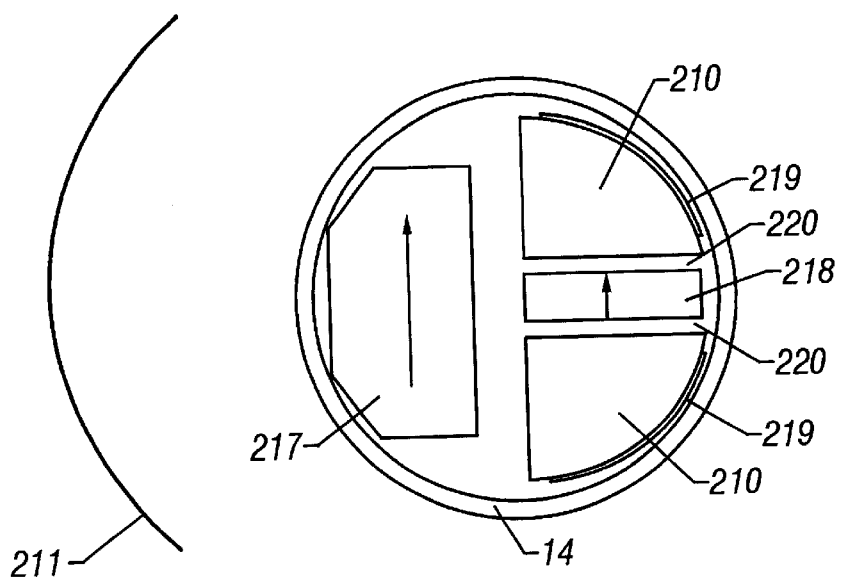
FIGS. 3, 3A and 3B show configurations of magnets, antenna and shield of the present invention for achieving the desired field configuration.

FIG. 3 schematically illustrates a preferred embodiment of the present invention wherein this shaping of the static and RF fields is accomplished. The tool cross-sectional view in FIG. 3 illustrates a main magnet 217, a second magnet 218, and a transceiver antenna, comprising wires 219 and core material 210. The arrows 221 and 223 depict the polarization (e.g., from the South pole to the North pole) of the main magnet 217 and the secondary magnet 218. A noteworthy feature of the arrangement shown in FIG. 3 is that the polarization of the magnets providing the static field is towards the side of the tool, rather than towards the front of the tool (the right side of FIG. 3) as in prior art devices. The importance of this rotated configuration is discussed below.

The second magnet 218 is positioned to augment the shape of the static magnetic field by adding a second magnetic dipole in close proximity to the RF dipole defined by the wires 219 and the soft magnetic core 210. This moves the center of the effective static dipole closer to the RF dipole, thereby increasing the azimuthal extent of the region of examination, the desirability of which has been discussed above. The second magnet 218 also reduces the shunting effect of the high permeability magnetic core 210 on the main magnet 217: in the absence of the second magnet, the DC field would be effectively shorted by the core 210. Thus, the second magnet, besides acting as a shaping magnet for shaping the static field to the front of the tool (the side of the main magnet) also acts as a bucking magnet with respect to the static field in the core 210. Those versed in the art would recognize that the bucking function and a limited shaping could be accomplished simply by having a gap in the core; however, since some kind of field shaping is required on the front side of the tool, in a preferred embodiment of the invention, the second magnet serves both for field shaping and for bucking. If the static field in the core 210 is close to zero, then the magnetostrictive ringing from the core is substantially eliminated.

Figure 3A:
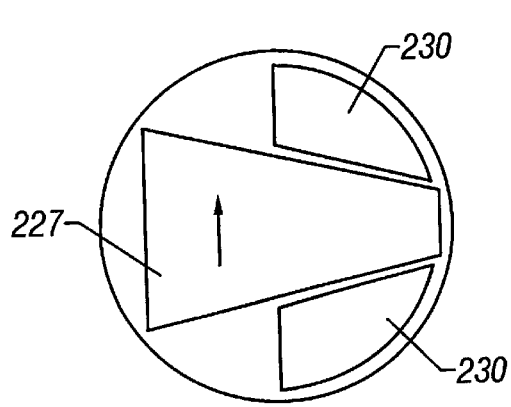
Figure 3B:
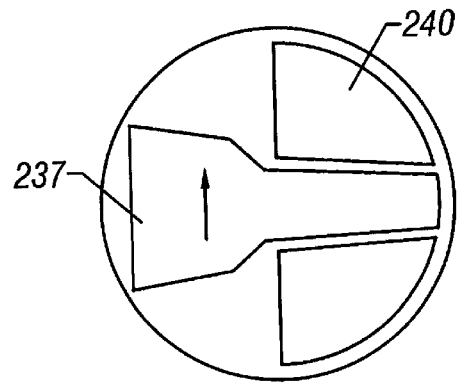

As noted above, within the region of investigation, the static field gradient is substantially uniform and the static field strength lies within predetermined limits to give a substantially uniform Larmor frequency. Those versed in the art would recognize that the combination of field shaping and bucking could be accomplished by other magnet configurations than those shown in FIG. 3. For example, FIG. 3A shows a single magnet 227 and magnetic core 230 that produces substantially the same static field as that produced by the combination of magnets 217 and 218 in FIG. 3. A substantially similar field configuration results from the arrangement in FIG. 3B with the magnet 237 and the core 240. What is being accomplished by the magnet arrangements in FIGS. 3, 3A and 3B is an asymmetry in the static magnetic field in a direction orthogonal to the direction of magnetization. In an optional embodiment of the invention (not shown) the second magnet is omitted.

Returning to FIG. 3, the transceiver wires 219 and core pieces 210 should preferably be separated as far as possible towards the sides of the tool. This separation increases the transceiver antenna efficiency by increasing the effective RF dipole of the antenna and augments the shape of the RF magnetic field isolines so that they better conform to the static magnetic field isolines. This separation is not possible in the Kleinberg design. The secondary magnet is preferably made of nonconducting material to minimize eddy currents induced by the RF field, thereby increasing the RF antenna efficiency.

The core is preferably made of a powdered soft magnetic material, other than ferrite. It preferably has a high saturation flux density and comprises particles of powdered material small enough to be transparent to the RF magnetic field. Such a material has been described in a co-pending application entitled "A Method and Apparatus of Using Soft Magnetic Material in a Nuclear Magnetic Resonance Probe" filed on Jun. 28, 2000, under Attorney Docket No. 584-13268, the contents of which are fully incorporated herein by reference.

Figure 4:
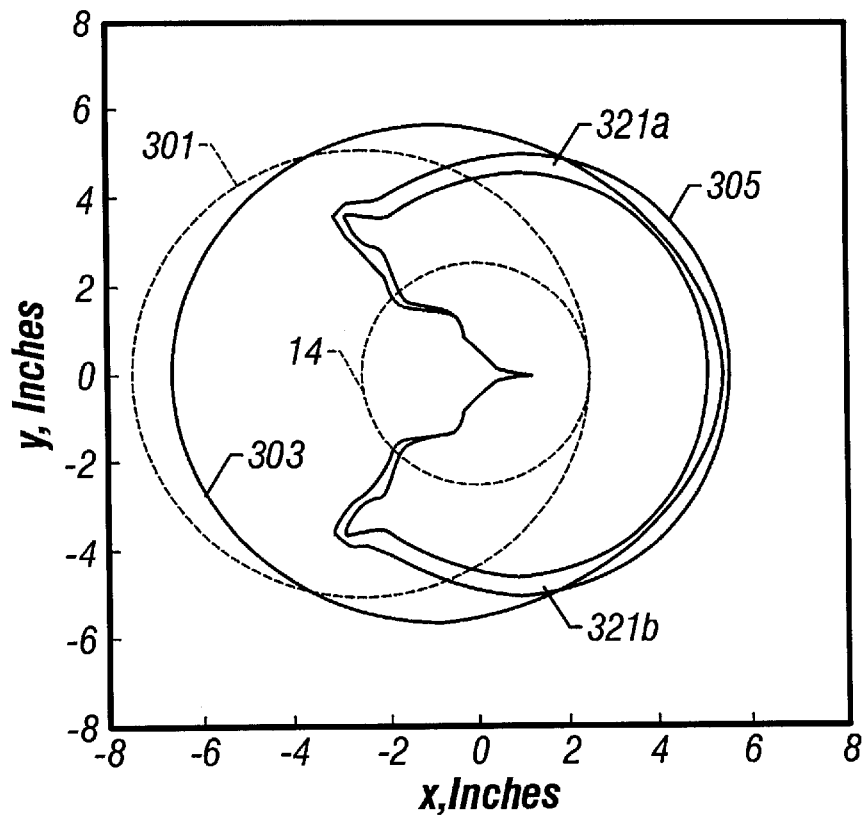
FIG. 4 illustrates the static and RF field isolines for the present invention.

Turning now to FIG. 4, results of a finite element modeling of the device illustrated in FIG. 3 are shown. The tool 14 having a diameter of 5 inches is shown within a borehole 301 with a diameter of 10 inches. The contour 303 denotes a static field strength $B_0$ between 184 Gauss and 186 Gauss. Within the region 305, the RF field varies by less than 10%, a suitable value for performing gradient NMR measurements. As can be seen the region of investigation characterized by the arc from 321a to 321b is much larger than in the arrangement shown in FIG. 2.

Figure 5:
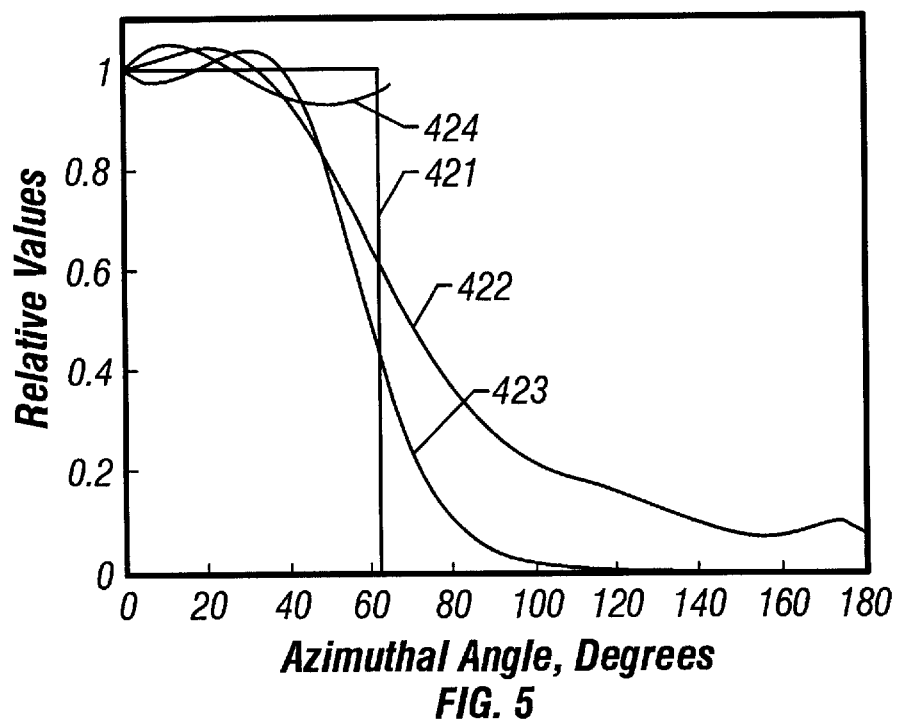
FIG. 5 shows the azimuthal variation of fields and sensitivity in the present invention.

The effective arc length is illustrated in FIG. 5. The abscissa is the azimuthal angle measured from the front of the receiver. For simplifying the illustration, only one half of the azimuthal distribution is shown. The line 423 is the azimuthal distribution of the received signal. The effective arc length 421 is the width of the rectangle having the same area as the received signal integrated over 180°. Also shown in FIG. 4 is the effective RF field 422 that is the product of the RF field magnitude and the cosine of the angle between the RF field and the static field. The gradient of the static magnetic field is denoted by 424 and indicates that the static magnetic field gradient is substantially constant in the region of investigation.

Figure 6:
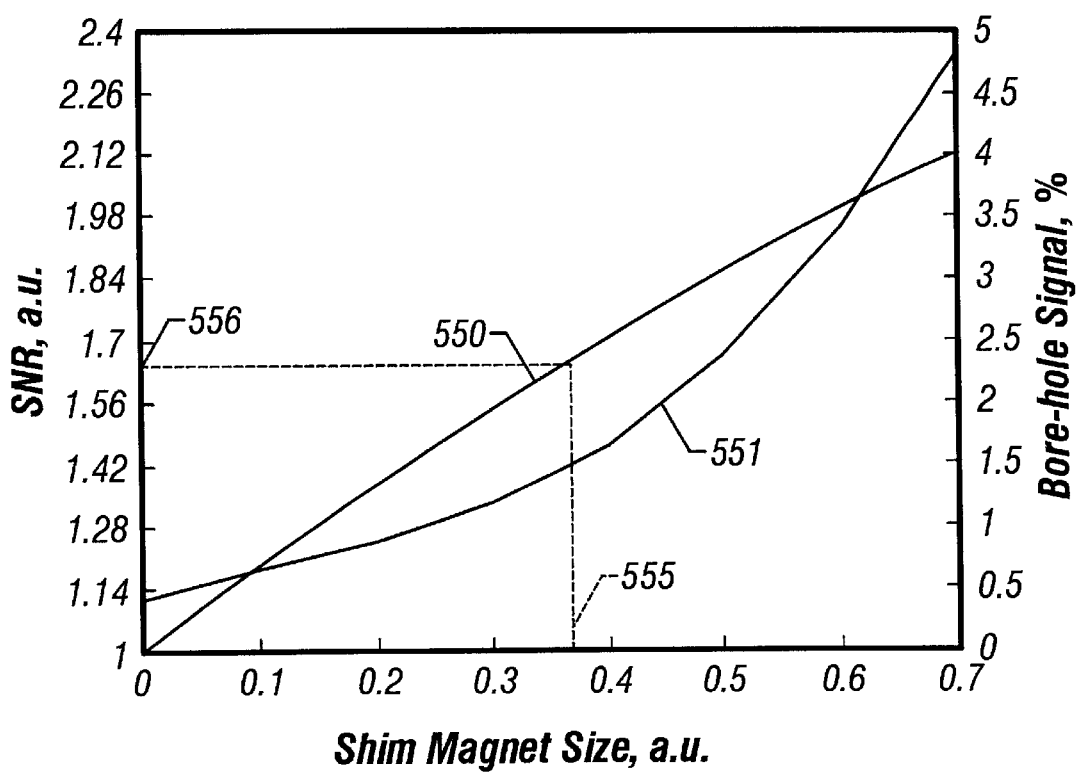
FIG. 6 shows the effect of varying the size of the second magnet in the present invention.

The selection of the size of the second magnet is based upon a finite element model of the magnet and antenna configuration as well as well as the NMR signal and noise calculations. This is illustrated in FIG. 6 that shows the SNR of the tool 550 and the signal 551 from the borehole as a function of the normalized second magnet size (abscissa). The second magnet size is normalized with respect to the gap length between the core segments 210 and a residual flux density of 1 Tesla is assumed. It is desirable to keep the borehole signal below a threshold such as 1.5%, giving a normalized second magnet size of approximately 0.37 (555) and a SNR of 1.63 (556). The main contribution to the improved SNR comes from the increase in arc length, with less of an contribution due to the increased field strength that results from a larger magnet size.

Figure 7A:
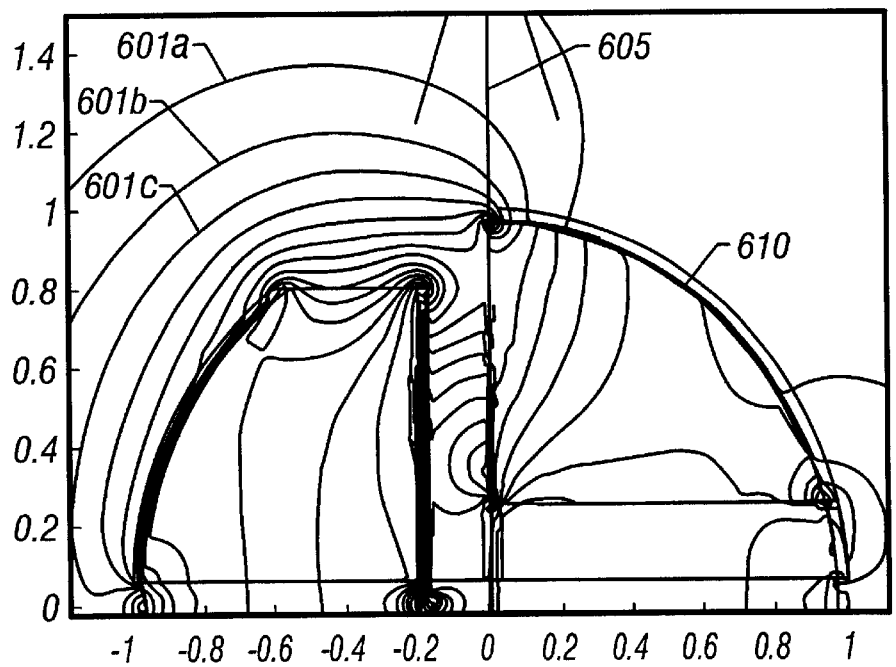
FIGS. 7a, 7b and 7c shows the static and RF field distribution for the tool configuration of FIG. 3.
Figure 7B:
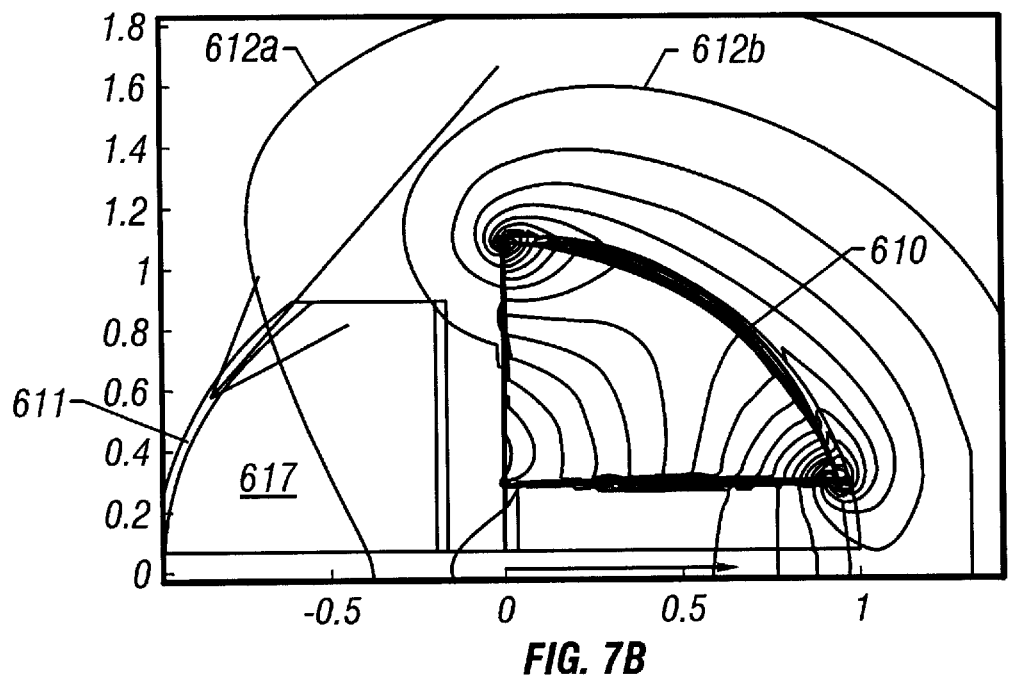
Figure 7C:
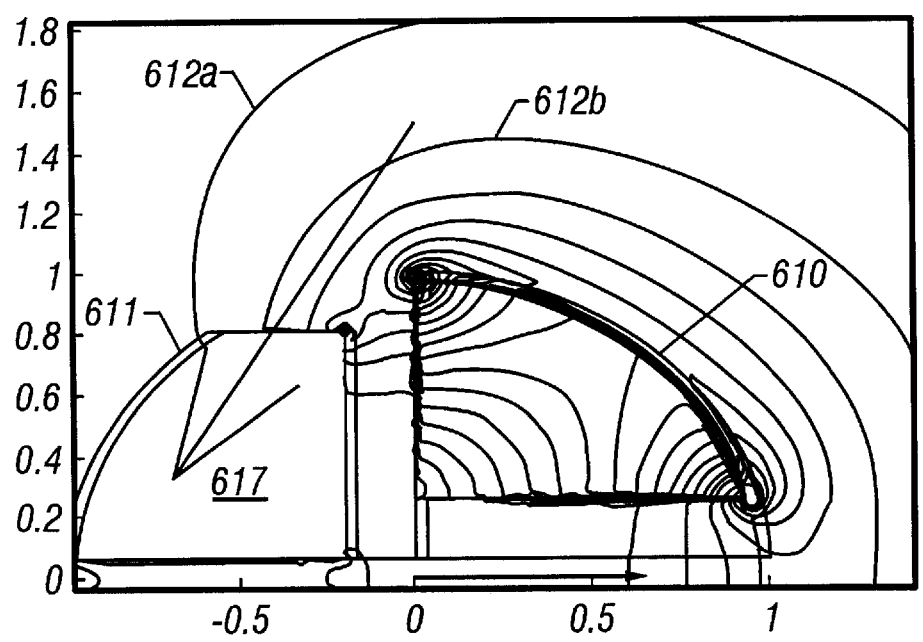

Turning now to FIG. 7a, the static field for one half of the magnet arrangement of FIG. 3 is shown. The contours 601a, 601b, . . . indicate the field strength and the arrow 605 indicates the direction of the static field at the origin. It may be seen in FIG. 7a that the static field is close to zero near the antenna wire position 610. This has the beneficial effect of reducing magnetostrictive ringing of the antenna. FIG. 7b shows the RF field isolines when the permanent magnet 617 is non-conducting. Even with a nonconducting permanent magnet, the RF field in the magnet is small, as indicated by the sparseness of the isofield lines 612a, 612b. . . near the permanent magnet. FIG. 7c shows the RF isofield lines when the permanent magnet is conducting, as in the preferred embodiment of the present invention.

The permanent magnets of the present invention are made of a conductive material such as Samarium-Cobalt. Conductive magnets, besides being able to provide a stronger static field, also act as a shield since the RF field has to go to zero in their vicinity. Ringing of the magnet is also less than for one made of non-conducting material.

Another beneficial effect is that the RF field near the shield is substantially perpendicular to the shield (not shown in FIGS. 7b and 7c). This means that the eddy currents induced in the shield 611by the RF field would be large compared to prior art devices such as Prammer, increasing the shielding effect with respect to borehole signals. As noted above, the RF shield is optional since the magnet itself provides considerable shielding of signals from the borehole.

While the foregoing disclosure is directed to the preferred embodiments of the invention, various modifications will be apparent to those skilled in the art. It is intended that all variations within the scope and spirit of the appended claims be embraced by the foregoing disclosure.

What is claimed is:

1. A Nuclear Magnetic Resonance (NMR) sensing apparatus comprising:
    (a) at least one primary (first) magnet to generate a static magnetic field in a volume containing materials sought to be analyzed, said at least one primary magnet having a longitudinal axis and being magnetized in a magnetization direction substantially perpendicular to said longitudinal axis, said magnetic field of said first magnet substantially that of an equivalent dipole magnet;
    (b) a radio frequency (RF) antenna for inducing a RF magnetic field in said volume and exciting nuclei therein and receiving signals from said excited nuclei, said RF magnetic field substantially that of a RF dipole orthogonal to the equivalent dipole magnet and displaced laterally therefrom; and
    (c) a second magnet having a magnetization substantially parallel to the magnetization of the at least one primary magnet, said second magnet disposed from the at least one primary magnet and the RF antenna for shaping said static magnetic field thereby defining an arcuate region of investigation in said volume wherein said static magnetic field has a field strength within predetermined limits and wherein said RF magnetic field has a substantially uniform field strength component orthogonal to the shaped static magnetic field.

2. The NMR apparatus of claim 1 wherein a magnetization direction of the at least one primary magnet defines a first side of the NMR apparatus.

3. The NMR apparatus of claim 2 wherein RF dipole is displaced in a direction orthogonal to said first side of the NMR apparatus, said displacement direction defining the front of the NMR apparatus.

4. The NMR apparatus of claim 3 wherein said arcuate region of investigation is substantially in the front of the NMR apparatus.

5. The NMR apparatus of claim 1 wherein said NMR apparatus is conveyed in a borehole and said arcuate region of examination subtends an angle at the center of the NMR apparatus between 90° and 135°.

6. The NMR apparatus of claim 1 wherein the RF antenna further comprises a gapped magnetic core.

7. The NMR apparatus of claim 6 wherein the gapped magnetic core is disposed between the second magnet and the antenna.

8. The NMR apparatus of claim 6 wherein said gapped magnetic core comprises a non-ferritic, powdered soft magnetic material.

9. The NMR apparatus of claim 3 further comprising an RF shield on a side of the apparatus opposite the front.

10. The NMR apparatus of claim 5, wherein the size of the second magnet is selected to increase the signal to noise ratio of the echo signals from said excited nuclei while maintaining an echo signal from a fluid within the borehole below a predetermined threshold.

11. The NMR apparatus of claim 1 wherein the arcuate region of investigation has a substantially uniform gradient of the static field.

12. The NMR apparatus of claim 1 wherein the at least one permanent magnet is made of a conducting material.

13. A Nuclear Magnetic Resonance (NMR) sensing apparatus comprising:
    (a) a magnet arrangement to generate a static magnetic field in a volume containing materials sought to be analyzed, said magnet arrangement having a shape and having a longitudinal axis and being magnetized in a direction substantially perpendicular to said longitudinal axis, the direction of magnetization defining a first side of the apparatus; and
    (b) a radio frequency (RF) antenna for inducing a RF magnetic field in said volume and exciting nuclei therein and receiving signals from said excited nuclei, said RF magnetic field substantially that of a RF dipole orthogonal
    to the direction of magnetization of the magnet arrangement; wherein the RF antenna is offset relative to the magnet arrangement along a direction substantially orthogonal to said direction of magnetization, and wherein the magnet arrangement is selected, to give an arcuate region of investigation in said volume wherein said static magnetic field has a field strength within predetermined limits and wherein said RF magnetic field has a substantially uniform field strength component orthogonal to the static magnetic field.

14. The NMR apparatus of claim 13 wherein the position of the RF antenna relative to the magnet arrangement defines a front of the apparatus and wherein said arcuate region of investigation is substantially in the front of the apparatus.

15. The NMR apparatus of claim 14 wherein said NMR apparatus is conveyed in a borehole and said arcuate region of examination subtends an angle at the center of the NMR apparatus between 90° and 135°.

16. The NMR apparatus of claim 13 wherein the RF antenna further comprises a gapped magnetic core disposed proximate to the antenna.

17. The NMR apparatus of claim 16 wherein said gapped magnetic core comprises a non-ferritic, powdered soft magnetic material.

18. The NMR apparatus of claim 14 further comprising an RF shield on a side of the apparatus opposite the front.

19. The NMR apparatus of claim 13 wherein the arcuate region of investigation further has a substantially uniform gradient of the static field.

20. The NMR apparatus of claim 13 wherein the magnet arrangement further comprises a permanent magnet made of conducting material.

21. The method of claim 13 wherein the NMR sensing apparatus is conveyed in a borehole containing a fluid and wherein said arcuate region of examination is substantially non-overlapping with the borehole.

22. A method of making Nuclear Magnetic Resonance (NMR) measurements comprising:
   (a) using at least one primary (first) magnet on an NMR tool to generate a static magnetic field in a volume containing materials sought to be analyzed, said at least one pry magnet having a longitudinal axis and being magnetized in a magnetization direction substantially perpendicular to said longitudinal axis, said magnetic field of said first magnet substantially that of an equivalent dipole magnet;
   (b) using a radio frequency (RF) antenna on the NMR tool for inducing a FMR magnetic field in said volume and exciting nuclei therein and receiving signals from said excited nuclei, said RF magnetic field substantially that of a RF dipole orthogonal to the equivalent dipole magnet and displaced laterally therefrom; and
   (c) placing a second magnet on the NMR tool in a position displaced away from the at least one primary magnet and towards the RF antenna for shaping said static magnetic field, thereby defining an arcuate region of investigation in said volume wherein said static magnetic field has a field strength within predetermined limits and wherein said RF magnetic field has a substantially uniform field strength component orthogonal to the shaped static magnetic field.

23. The method of claim 22 wherein RF dipole is displaced in a direction orthogonal to said magnetization direction, said displacement direction defining the front of the NMR apparatus.

24. The method of claim 22 further comprising using a gapped core with the antenna for increasing the efficiency thereof.

25. The method of claim 24 comprising using the second magnet for reducing magnetostrictive ringing of the gapped core and the antenna.

26. The method of claim 22 further comprising using the NMR apparatus in a borehole in a subterranean formation for determining a parameter of interest of the formation.

27. The method of claim 26 further comprising selecting a size for the second magnet for increasing the signal to noise ratio of the echo signals from said excited nuclei while maintaining an echo signal from a fluid within the borehole below a predetermined threshold.

28. The method of claim 26 further comprising positioning the second magnet and selecting a size thereof for obtaining a value of the angle subtended by said arcuate region of examination at the center of the NMR tool between 90° and 135°.

29. The method of claim 22 further comprising using an RF shield on a back side of the NMR tool opposite the front of the tool for attenuating signals from said back side.

30. The method of claim 22 further comprising using a conducting material for the at least one of (i) the at least one primary magnet, and, (ii) the second magnet.

31. The method of claim 26 wherein said arcuate region is substantially non-overlapping with the borehole.

32. A method of making Nuclear Magnetic Resonance (NMR) measurements comprising:
   (a) using a magnet arrangement on an d tool to generate a static magnetic field in a volume containing materials sought to be analyzed, said magnet arrangement having a longitudinal axis and being magnetized in a magnetization direction substantially perpendicular to said longitudinal axis;
   (b) positioning an RF antenna on the NMR tool along a direction orthogonal to said magnetization direction, thereby defining a front of the NMR tool;
   (c) using the radio RF antenna on the NMR tool for inducing a NMR magnetic field in said volume and exciting nuclei therein and receiving signals from said excited nuclei, said RF magnetic field substantially tat of a RF dipole orthogonal to said magnetization direction; and
   (d) selecting the magnet arrangement and the position of the RF antenna relative to the magnet arrangement and defining an arcuate region of investigation in front of the tool in said volume wherein said static magnetic field has a field strength within predetermined limits and wherein said RF magnetic field has a substantially uniform field strength component orthogonal to the static magnetic field.

33. The method of claim 32 wherein selecting said magnet arrangement further comprises one of:
   (i) selecting a main (first) magnet having a dipole magnetic field and a second magnet displaced towards the front of the tool for defining the static field. and
   (ii) selecting a shaped magnet for defining the static field.

34. The method of claim 32 further comprising using a RF shield for attenuating NMR signals from a side of the tool opposite the front.

35. The method of claim 32 further comprising conveying the NMR tool in a borehole and positioning the tool eccentrically in the borehole with said front face proximate to a wall of the borehole.

36. The method of claim 33 wherein an angle subtended by said arcuate region at the center of the NMR tool is between 90° and 135°.

* * * * *